(12) United States Patent
Proksa

(10) Patent No.: US 7,627,080 B2
(45) Date of Patent: Dec. 1, 2009

(54) QUANTITATIVE MATERIAL DECOMPOSITION FOR SPECTRAL CT

(75) Inventor: Roand Proksa, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 25 days.

(21) Appl. No.: 12/067,184

(22) PCT Filed: Sep. 12, 2006

(86) PCT No.: PCT/IB2006/053227

§ 371 (c)(1),
(2), (4) Date: Mar. 18, 2008

(87) PCT Pub. No.: WO2007/034359

PCT Pub. Date: Mar. 29, 2007

(65) Prior Publication Data

US 2008/0253504 A1 Oct. 16, 2008

(30) Foreign Application Priority Data

Sep. 22, 2005 (EP) .................................. 05108746

(51) Int. Cl.
*A61B 6/03* (2006.01)

(52) U.S. Cl. ........................................................ 378/6

(58) Field of Classification Search .................. 378/4, 378/6, 86, 88
See application file for complete search history.

(56) References Cited

U.S. PATENT DOCUMENTS

| 2003/0147502 | A1 | 8/2003 | Heismann et al. |
| 2004/0101088 | A1* | 5/2004 | Sabol et al. ..................... 378/4 |
| 2004/0223585 | A1 | 11/2004 | Heismann et al. |
| 2005/0094769 | A1 | 5/2005 | Heismann et al. |

OTHER PUBLICATIONS

Goh, K. L., et al.; Energy-dependent systematic errors in dual-energy x-ray CT; 1997; IEEE Trans. on Nuclear Science; 44(2)212-217.
Goh, K. L., et al.; Correction of energy-dependent systematic errors in dual-energy X-ray CT using a basis material coefficients transformation method; 1997; IEEE Trans. on Nuclear Science; 44(6)2419-2424.
Hassler, U., et al.; X-ray dual-energy calibration based on estimated spectral properties of the experimental system; 1998; IEEE Trans. on Nuclear Science; 45(3)1699-1712.
Kalender, W. A., et al.; Evaluation of a prototype dual-energy computed tomographic apparatus. I. Phantom studies; 1986; Am. Assoc. Phys. Med.; 13(3)334-339.

* cited by examiner

*Primary Examiner*—Chih-Cheng G Kao

(57) ABSTRACT

A data processing method for use in an imaging system is described. The method includes determining a special footprint of an unknown mixture of substances from a first region and using the spectral footprint to decomposition of second region.

11 Claims, 3 Drawing Sheets

QUANTITATIVE MATERIAL DECOMPOSITION FOR SPECTRAL CT

Figure 1:
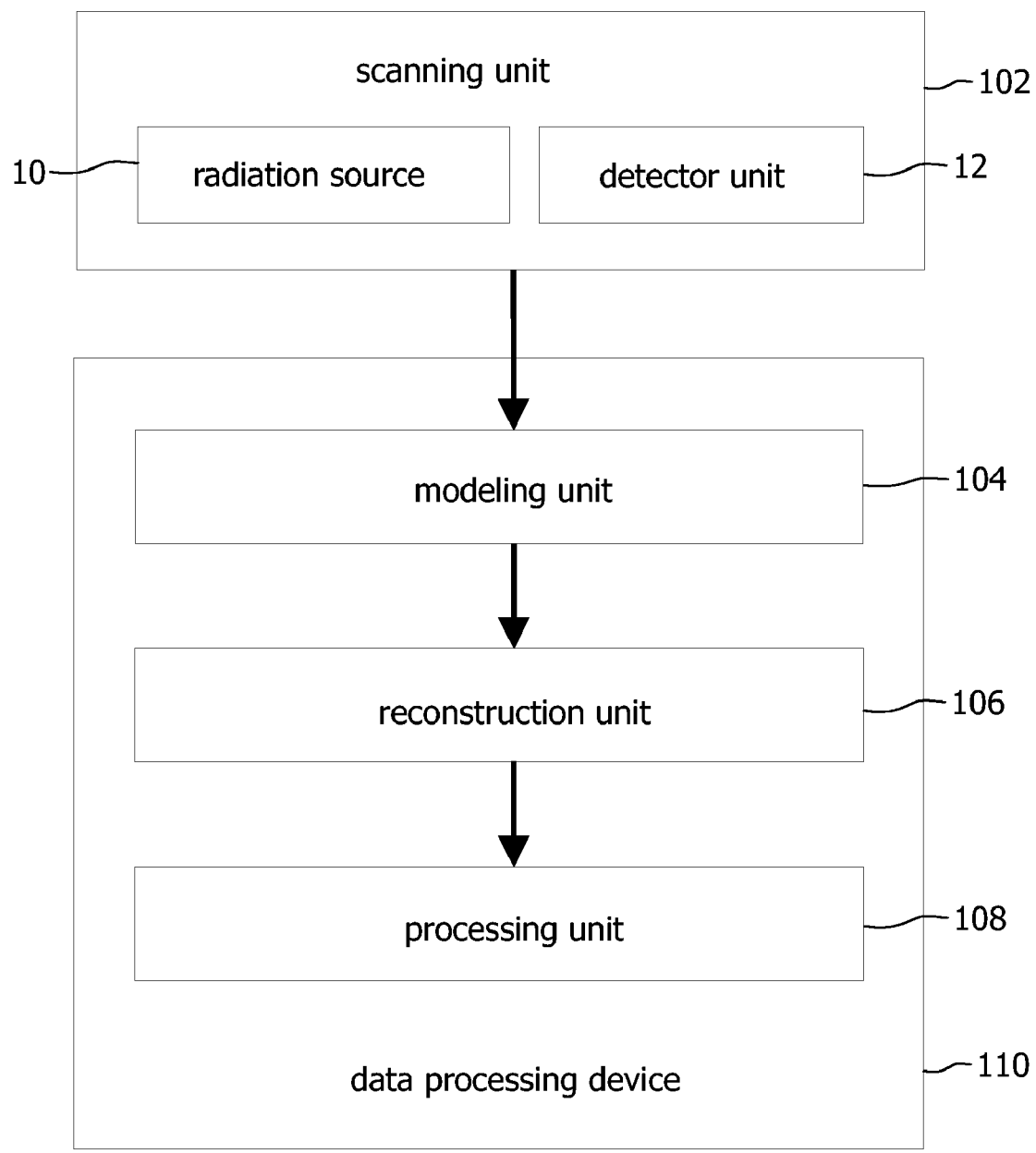

The present invention relates to a CT system for determining the quantitative material concentrations of the components in a region of interest of an object with known Compton attenuation coefficients and photoelectric attenuation coefficients for said components. Further the present invention relates to a data processing device for use in such a CT system and to a corresponding data processing method. Still further, the present invention relates to a computer program for implementing said data processing method on a computer.

To provide quantitative material decomposition has already been an object of CT technology (computered tomography technology) in the past. A well-known method for so-called dual energy analysis is the subtraction (or division) of images acquired at different energies to enhance the contrast. However, the method is heuristic and a physical or biological meaning of the images is not defined. Furthermore, dual energy CT is capable to present two images with equivalent material compositions. An often used decompositon uses soft tissue and bone equivalence, like it is, for instance, described in Kalender, W. A. et al., "Evaluation of a Prototype Dual Energy Computer Tomographic Apparatus. I. Phantom Studies", Medical physics, Vol. 13, No. 3, May/June 1986, pages 334 to 339. However, a high value in the bone image does not mean that there is really bone. It only means that the presented combination of bone and soft tissue would yield the same measurements.

The explanatory power of such results is marginal since this method leaves a wide range of interpretations. Thus, there is a lack of proper techniques for quantitative material decomposition which provide adequate results.

It is thus an object of the present invention to provide a CT system which improves the quality and explanatory power of quantitative material decomposition. Further, a corresponding data processing device and data processing method shall be provided.

The object is achieved according to the present invention by a CT system as defined in claim 1 comprising:

- a scanning unit having a radiation source and a detector unit for acquisition of spectral CT projection data from said region of interest,
- a modeling unit for obtaining a photoelectric effect projection data set and a Compton effect projection data set by decomposing said spectral CT projection data set by means of respective models of photoelectric effect and Compton effect,
- a reconstruction unit for reconstructing a photoelectric effect image and a Compton effect image of said region of interest from said photoelectric effect projection data set and Compton effect projection data set,
- a processing unit for determining the concentrations of said components in said region of interest by solving a system of equations obtained by equating said photoelectric effect image data with the accumulated products of said concentrations and photoelectric attenuation coefficients for said components and equating said Compton effect image data with the accumulated products of said concentrations and Compton attenuation coefficients for said components.

An appropriate data processing device for use in such a CT system and a corresponding data processing method are defined in claims 8 and 9. A computer program which may be stored on a record carrier for implementing said data processing method on a computer is defined in claim 10. Preferred embodiments of the invention are defined in the dependent claims.

The present invention is based on the idea to use spectral CT data for quantitative material decomposition and further on the idea, that a number m of measurable physical effects in a region of interest allows to determine the concentrations of (m+1) components in said region of interest. It is assumed that a spectral CT scanner acquires projection data with different spectral coding. These data can be fitted to a physical model of the object. The physical model contains several physical effects such as Compton effect, photoelectric effect and K-edge effect. If K-edges are identified, the related decomposition is directly achieved by dividing the physical model of the objects into the physical models of the effects. The two model parameters of the remaining effects (Compton effect and photoelectric effect) allow to decompose a mixture of the remaining at most three components. Any ingredient i with density $\rho_i$, atomic weight $A_i$ and atomic number $Z_i$ has Compton and photoelectric attenuation of $$\mu_i^{compton}(E) = K_1 \rho_i A_i^{-1} Z_i f_{KN}(E)$$

$$\mu_i^{photo}(E) = K_2 \rho_i A_i^{-1} Z_i^n E^{-3}.$$

$K_1$ and $K_2$ are constant, n has a value of about 4, and $f_{KN}(E)$ is the so-called integrated Klein-Nishina function. The energy independend attenuation contributions are referred to as $\eta_i^{compton}$ and $\eta_i^{photo}$, hereinafter, with:

$$\eta_i^{compton} = \rho_i A_i^{-1} Z_i$$

$$\eta_i^{photo} = \rho_i A_i^{-1} Z_i^n.$$

If there are three ingredients with relative volumetric concentrations $c_1$, $c_2$ and $c_3 = (1-c_1-c_2)$ the following system of equations is obtained:

$$\eta_{mixture}^{compton} = c_1 \eta_1^{compton} + c_2 \eta_2^{compton} + (1-c_1-c_2) \eta_3^{compton}$$

$$\eta_{mixture}^{photo} = c_1 \eta_1^{photo} + c_2 \eta_2^{photo} + (1-c_1-c_2) \eta_3^{photo}$$

This system of equations can be solved to the two unknowns ($c_1$ and $c_2$) on a per voxel basis or with at least $\chi^2$ fit over a region of interest. The materials whose concentrations are to be determined can be elements, molecules or any known mixture.

In a preferred embodiment the number of the components whose concentrations are to be determined is restricted to at most three. Thus, the determination of the concentrations of the components is easier since only two physical effects have to be considered. However, in another embodiment the number of said components is restricted to at most four wherein for at least one of said components the K-edge effect is known and wherein said modeling unit is adapted for additionally obtaining a K-edge projection data set by using a respective model of K-edge effect corresponding to said at least one component and thereby indicating the concentration of said at least one component. Thus, it is possible to consider an additional component. Advantageously, said at least one component with known K-edge effect is indicated by a contrast agent, particularly Iodine or Gadolinium, which is injected into said object. These contrast agents feature readily identifiable K-edge effects and thus facilitate the determination of the concentration of said additional component.

Additionally, the invention can be used to measure a "spectral footprint" of unknown mixtures that can be further used for improved analysis. If in an example with a contrast agent (CA) it is possible to define a region that contains only CA and one another component such as blood, e.g. a chamber, it can be decomposed into the component (blood) and CA and allows a quantitative measure of the CA concentration. The mixture (blood, CA) can be used as a spectral footprint for the decomposition of other areas. The other area can be decomposed into blood-CA mixture, soft tissue and calcium or into blood-CA mixture, soft tissue and metal for example. The quality of the decomposition depends on the dissimilarity of the spectral footprint of the components and improves if the density and/or the atomic number differences are large. By measuring a "spectral footprint" the invention offers more flexibility and allows to determine the concentrations of the components even if there are more than three components/subcomponents.

In an embodiment of the present invention at least one of said components (referred to as a compound component, hereinafter) is represented by one or more subcomponents. Thus, a compound component may contain a mixture of subcomponents, for example, in case that Compton attenuation coefficients and photoelectric attenuation coefficients are only known for the mixture and not for each subcomponent. This also allows to determine the concentration of a compound component in a region of interest if the total number of ingredients in a region of interest in the form of subcomponents is not restricted to three, in case only Compton attenuation coefficients and photoelectric attenuation coefficients are known, or is not restricted to four, in case for at least one of said components the K-edge effect is known. Advantageously said known Compton attenuation coefficients and photoelectric attenuation coefficients of said compound component represented by one or more subcomponents are obtained by said modeling unit as said photoelectric effect projection data set and said Compton effect projection data set, respectively. Thus, even if the Compton attenuation coefficient and the photoelectric attenuation coefficient of said at least one compound component represented by one or more subcomponents are unknown the invention allows to determine the concentration of the components in a region of interest by determining the Compton attenuation coefficient and the photoelectric attenuation coefficient of said compound component.

Figure 2:
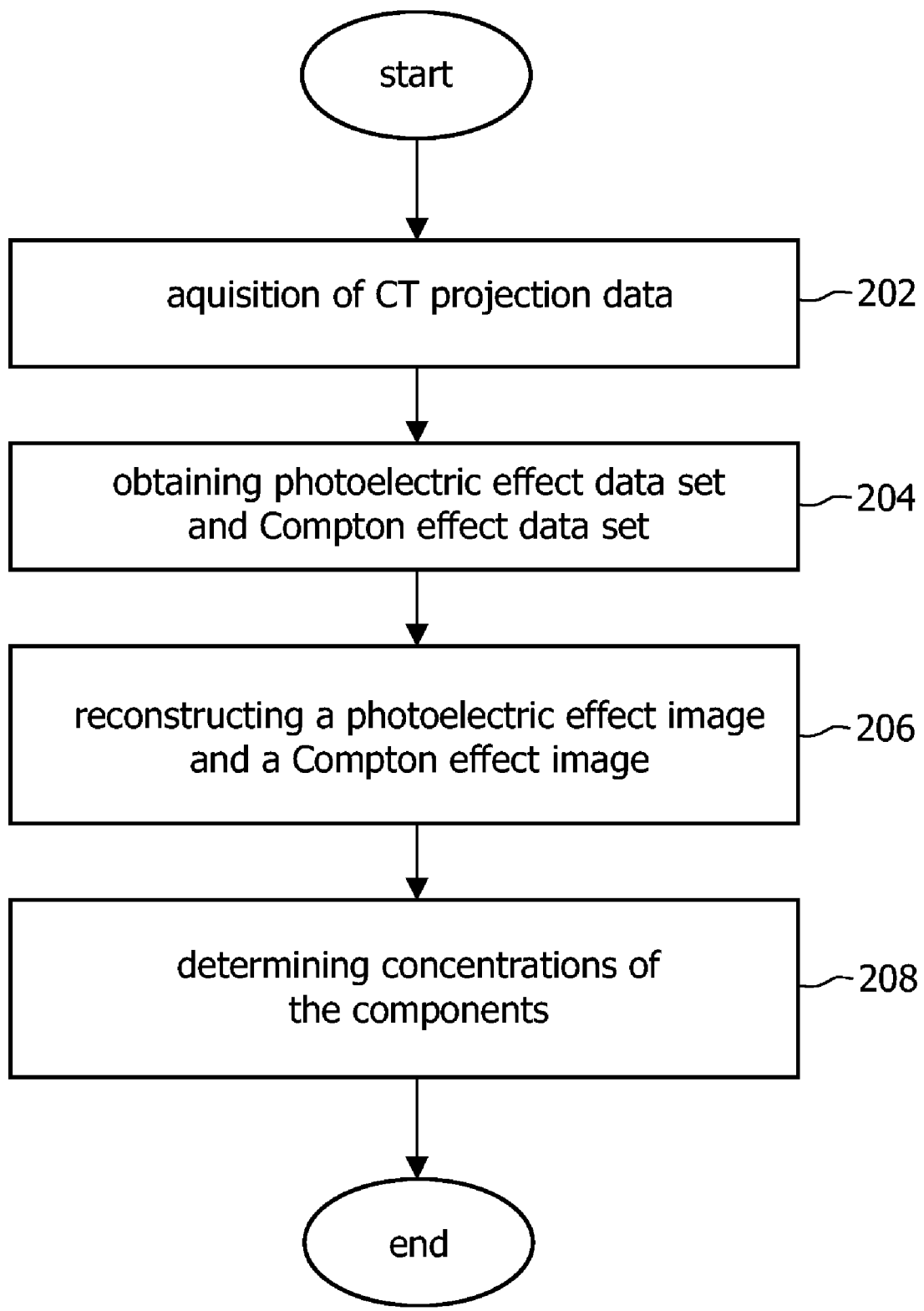
Figure 3:
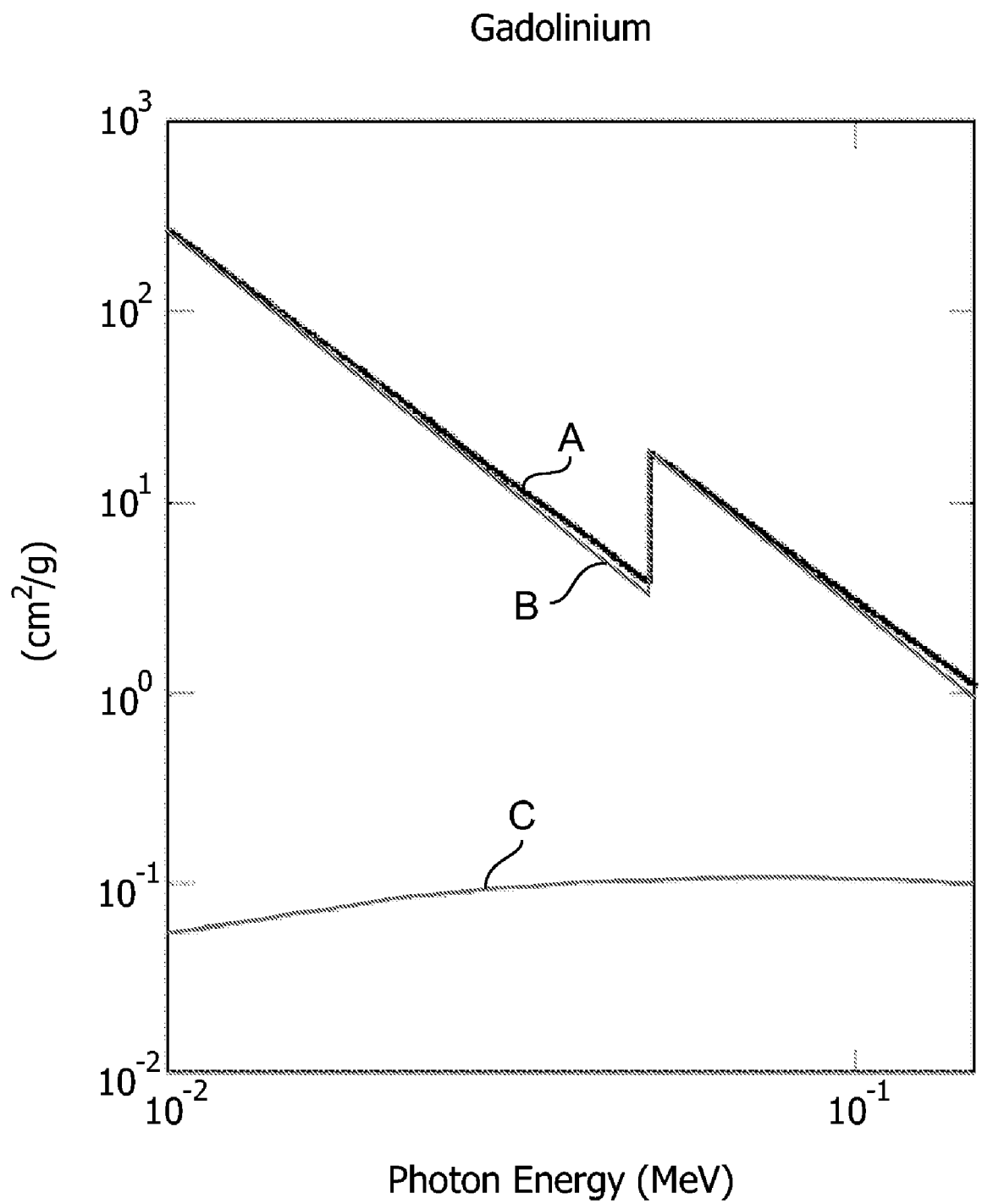

The invention will now be described in more detail by way of embodiments with reference to the drawings in which FIG. 1 shows a block diagram of a CT system according to the invention, FIG. 2 shows a flowchart of a data processing method according to the invention, FIG. 3 shows a graph representing the attentuation spectrum of Gadolinium.

The first embodiment describes a device and a method for determining the quantitative material concentrations of three components in a region of interest of an object. Compton attenuation coefficients and photoelectric attenuation coefficients for said components are known.

FIG. 1 shows a spectral CT system according to the first embodiment comprising a scanning unit 102, a modeling unit 104, a reconstruction unit 106 and a processing unit 108. Said scanning unit 102 comprises a radiation source 10 and a detector unit 12. Said modeling unit, said reconstruction unit 106 and said processing unit 108 compose a data processing device 110.

As shown in FIG. 2 in a first step 202 said scanning unit 102 acquires spectral CT projection data of an object or of a region of interest of said object. To achieve this, said radiation source 10 of said scanning unit 102 emits a radiation beam of spectral energy towards said detector unit 12. Said detector unit 12 receives the respective energy signals diminished by the attenuation caused during the passage of the radiation beam through the object. In this first embodiment the detector unit 12 is constituted by an energy-resolving X-ray detector. Such energy-resolving X-ray detector may be commercially available in the near future. It is also possible to use a conventional dual layer detector unit 12 as said spectral CT projection data is provided to said modeling unit 104.

In a second step 204 said modeling unit 104 obtains a photoelectric effect projection data set and a Compton effect projection data set which correspond to the spatial distribution of the attenuation caused by photoelectric effect and Compton effect, respectively. Said photoelectric effect projection data set and said Compton effect projection data set are obtained by decomposing said spectral CT projection data set acquired by said step 202 with scanning unit 102. A typical physical model which includes the measurement has the form $$M_j \approx \int S_j(E) e^{-\int_R (\mu^{photo}(x,E) + \mu^{compton}(x,E)) ds} dE$$

where $M_j$ is the result of measurement j, acquired with a scanning unit channel that has the spectral sensitivity $S_j(E)$. The measurement was performed along a ray R on which the energy (E) and spatial (x) dependent linear attenuations $\eta^{photo}(x, E)$, $\eta^{compton}(x, E)$ were integrated (ds). The modeling unit 104 derives the energy independend quantities $$\int_R \eta^{photo}(x) ds \text{ and } \int_R \eta^{compton}(x) ds.$$

In a third step 206 said reconstruction unit 106 reconstructs two images $\eta^{photo}(x)$ and $\eta^{compton}(x)$ from the calculated line integrals $$\int_R \eta^{photo}(x) ds \text{ and } \int_R \eta^{compton}(x) ds.$$

In a fourth step 208 said processing unit 108 determines the concentrations of said three components in said region of interest. This is achieved by solving the following system of equations:

$$\eta_{mixture}^{compton}(x) = c_1(x)\eta_1^{compton}(x) + c_2(x)\eta_2^{compton}(x) + (1-c_1(x)-c_2(x))\eta_3^{compton}(x)$$

$$\eta_{mixture}^{photo}(x) = c_1(x)\eta_1^{photo}(x) + c_2(x)\eta_2^{photo}(x) + (1-c_1(x)-c_2(x))\eta_3^{photo}(x)$$

$\eta^{Compton}(x)$ and $\eta^{photo}(x)$ correspond as above to said photoelectric effect projection data set and Compton effect projection data set, which correspond to the spatial distribution of the attenuation caused by photoelectric effect and Compton effect. $c_1(x)$ and $c_2(x)$ represent the concentrations of component 1 and component 2 at point x to be determined, respectively. A concentration $c_3(x)$ of a third component 3 is obtained by subtracting $c_1(x)$ and $c_2(x)$ from 1 ($c_3(x)=1-c_1(x)-c_2(x)$) since there are only three components in the region of interest. $\eta_1^{Compton}(x)$, $\eta_2^{Compton}(x)$ and $\eta_3^{Compton}(x)$ correspond to the Compton attenuation coefficients of said components, respectively, which are known and can, for example, be acquired by so-called NIST tables. $\eta_1^{photo}(x)$, $\eta_2^{photo}(x)$ and $\eta_3^{photo}(x)$ correspond to the photoelectric attenuation coefficients of said components, respectively, which are known as well and can also, for example, be obtained by so-called NIST (National Institute of Standards and Technology) tables. The above system of equations can be solved to the two unknowns ($c_1(x)$ and $c_2(x)$), and $c_3(x)$ can be determined therefrom. Said concentrations $c_1(x)$, $c_2(x)$, $c_3(x)$ of said three components are obtained on a per voxel basis or with a least squares fit over the region of interest.

A second embodiment describes a spectral CT system for determining the quantitative material concentrations of four components in a region of interest of an object with known Compton attenuation coefficients and photo electric attenuation coefficients for said components and with known K-edge effect for at least one of said components. In this second embodiment said at least one component with known K-edge effect is Gadolinium with a K-edge effect at about 60 keV. A graph representing the attentuation spectrum of Gadolinium is shown in FIG. 3 with attentuation (1/cm) per mass density (g/cm3). FIG. 3 shows the total attenuation with coherent scattering A, the attenuation caused by the photo electric effect B, and the attenuation caused by Compton effect (incoherent scattering) C. But any other material with a K-edge effect which is applicable to differ from other materials in the scanned object may be used. This may be, for example, any other contrast agent, such as, for example, Iodine which has a K-edge effect at about 30 keV.

The second embodiment differs from the first embodiment in that in said second step 204 said modeling unit 104 is adapted to additionally obtain a K-edge projection data set corresponding to the attenuation caused by K-edge effect. Said K-edge projection data set is obtained by decomposing said spectral CT projection data acquired by said scanning unit 102 by means of respective models of photoelectric effect, Compton effect and K-edge effect, as follows:

$$\mu^{total}(E) = \mu^{photo}(E) + \mu^{compton}(E) + \mu^{K-edge}(E).$$

The above-mentioned typical physical model is extended with the related absorption of the contrast agent $$M_j \approx \int S_j(E) e^{-\int_R (\mu^{photo}(x,E) + \mu^{compton}(x,E) + c_4(x)\mu^{K-edge}(E)) ds} dE$$

A typical spectrum of Gadolinium $\mu^{K-edge}(E)$ is shown in FIG. 3. It is given in arbsorption per mass density. The relative concentration of Gadolinium $c_4(x)$ in a mixture becomes the third model parameter that is calculated by the modeling unit 104. As for the photo and Compton effect projection data, the result is given by a line integral $$\int_R c_4(x) ds.$$

The reconstruction unit 106 performs an additional reconstruction by calculating $c_4(x)$. Said photoelectric effect image, said Compton effect image and said concentration $c_4(x)$ of Gadolinium, i.e. said fourth component, are provided to said processing unit 108.

Further in this second embodiment in said fourth step 208 said processing unit 108 is adapted to determine the concentrations of the remaining three components in said region of interest. This is achieved by solving the following system of equations:

$$\eta^{compton}(x) = c_1(x)\eta_1^{compton}(x) + c_2(x)\eta_2^{compton}(x) + (1 - c_1(x) - c_2(x) - c_4(x))\eta_3^{compton}(x)$$

$$\eta^{photo}(x) = c_1(x)\eta_1^{photo}(x) + c_2(x)\eta_2^{photo}(x) + (1 - c_1(x) - c_2(x) - c_4(x))\eta_3^{photo}(x)$$

Same variables denote same terms as in embodiment 1. Additionally, $c_4(x)$ represents the concentration of said fourth component. A concentration $c_3(x)$ of a third component 3 is obtained by subtracting $c_1(x)$, $c_2(x)$ and $c_4(x)$ from 1 ($c_3(x) = 1 - c_1(x) - c_2(x) - c_4(x)$) since there are only four components in the region of interest. The above system of equations can be solved to the two unknowns ($c_1(x)$ and $c_2(x)$) and $c_3(x)$ can be determined therefrom. Said concentrations $c_1(x)$, $c_2(x)$, $c(x)_3$ and $c_4(x)$ of said four components are obtained on a per voxel basis or with a least squares fit over the region of interest.

A third embodiment describes a CT system for determining a so-called spectral footprint of a component (referred to as a compound component, hereinafter) represented by one or more subcomponents, e.g. elements, molecules or a mixture. A subcomponent means a material, for which at least photoelectric attenuation coefficient and Compton attenuation coefficient are to be determined for any reason, for example, because neither photoelectric attenuation coefficient nor Compton attenuation coefficient nor K-edge effect are known for a material or for a mixture of materials. A spectral footprint means the photoelectric attenuation coefficient and Compton attenuation coefficient of said compound component determined by said CT system before determining the concentrations of the components.

The third embodiment can be realized in two different ways. The first way is to use said CT system to image a sample of the component. In this case, the reconstructed images $\eta^{photo}(x)$ and $\eta^{compton}(x)$ represent the spectral footprint of the compound component and can be used in further examinations to represent one of three or four components, respectively. The second way is to select a region of interest in the reconstruction images that contains a homogenous distribution of the compound component. The mean value of the images $\eta^{photo}(x)$ and $\eta^{compton}(x)$ in this area can be used as the spectral footprint for the analysis in other areas.

It is possible to combine the features of above embodiments and in this way to determine the concentrations of plural components and/or to determine spectral footprints of plural components at once in case the concentrations of said components are known. For example embodiment 3 and embodiment 2 can be combined to determine a spectral footprint of an unknown component in case there is an unknown component and a component with known photoelectric attenuation coefficient, Compton attenuation coefficient and K-edge effect, such as a CA, in a region of interest.

The invention claimed is:

1. A CT system for determining the quantitative material concentrations of the components in a region of interest of an object with known Compton attenuation coefficients and photoelectric attenuation coefficients for said components comprising:

a scanning unit having a radiation source and a detector unit for acquisition of spectral CT projection data from said region of interest;

a modeling unit for obtaining a photoelectric effect projection data set and a Compton effect projection data set by decomposing said spectral CT projection data set by means of respective models of photoelectric effect and Compton effect;

a reconstruction unit for reconstructing a photoelectric effect image and a Compton effect image of said region of interest from said photoelectric effect projection data set and Compton effect projection data set;

a processing unit for determining the concentrations of said components in said region of interest by solving a system of equations obtained by equating said photoelectric effect image data with the accumulated products of said concentrations and photoelectric attenuation coefficients for said components and equating said Compton effect image data with the accumulated products of said concentrations and Compton attenuation coefficients for said components.

2. The CT system as claimed in claim 1, wherein the number of said components is restricted to at most three.

3. The CT system as claimed in claim 1, wherein the number of said components is restricted to at most four with known K-edge effect for at least one of said components and wherein said modeling unit is adapted for additionally obtaining a K-edge projection data set by using a respective model of K-edge effect corresponding to said at least one component and thereby indicating the concentration of said at least one component.

4. The CT system as claimed in claim 3, wherein said at least one component is indicated by a contrast agent injected into said object.

5. The CT system as claimed in claim 4, wherein said contrast agent is Iodine or Gadolinium.

6. The CT system as claimed in claim 1, wherein at least one of said components is represented by one or more sub-components.

7. The CT system as claimed in claim 6, wherein said known Compton attenuation coefficients and photoelectric attenuation coefficients of said at least one component are obtained by said modeling unit as said photoelectric effect projection data set and said Compton effect projection data set, respectively.

8. A data processing device for use in a CT system for determining the quantitative material concentrations of the components in a region of interest of an object with known Compton attenuation coefficients and photoelectric attenuation coefficients for said components, said data processing device being provided with spectral CT projection data of said region of interest, said spectral CT projection data being obtained from a scanning unit, comprising:
a modeling unit for obtaining a photoelectric effect projection data set and a Compton effect projection data set by decomposing said spectral CT projection data set by means of respective models of photoelectric effect and Compton effect;
a reconstruction unit for reconstructing a photoelectric effect image and a Compton effect image of said region of interest from said photoelectric effect projection data set and Compton effect projection data set;
a processing unit for determining the concentrations of said components in said region of interest by solving a system of equations obtained by equating said photoelectric effect image data with the accumulated products of said concentrations and photoelectric attenuation coefficients for said components and equating said Compton effect image data with the accumulated products of said concentrations and Compton attenuation coefficients for said components.

9. A data processing method for use in a CT system for determining the quantitative material concentrations of the components in a region of interest of an object with known Compton attenuation coefficients and photoelectric attenuation coefficients for said components, said data processing method being provided with CT projection data of said region of interest, said CT projection data being obtained from a scanning unit, comprising the steps of:
obtaining a photoelectric effect projection data set and a Compton effect projection data set by decomposing said spectral CT projection data set by means of respective models of photoelectric effect and Compton effect;
reconstructing a photoelectric effect image and a Compton effect image of said region of interest from said photoelectric effect projection data set and Compton effect projection data set;
determining the concentrations of said components in said region of interest by solving a system of equations obtained by equating said photoelectric effect image data with the accumulated products of said concentrations and photoelectric attenuation coefficients for said components and equating said Compton effect image data with the accumulated products of said concentrations and Compton attenuation coefficients for said components.

10. A computer-readable medium encoded with a computer program that causes a computer to perform the steps of the method as claimed in claim 9 when said computer program is run on a computer.

11. A data processing method for use in a CT system comprising:
determining a spectral footprint of an unknown mixture of substances from a first region or object; and
using the spectral footprint of the unknown mixture of substances for the decomposition of a second region or object;
wherein the decomposition of the second region or object comprises:
obtaining a photoelectric effect projection data set and a Compton effect projection set by decomposing a spectral CT projection data set with respective models of photoelectric effect and Compton effect;
reconstructing a photoelectric effect image and a Compton effect image of the second region or object from the photoelectric effect projection data set and the Compton effect projection data set; and
determining the concentration of components in the second region or object by solving a system of equations obtained by equating the photoelectric effect image data with accumulated products of the concentrations and photoelectric attenuation coefficients for the components and equating the Compton effect image data with accumulated products of the concentrations and Compton attenuation coefficients for the components.

* * * * *